United States Patent
Zoeller et al.

(12) 
(10) Patent No.: US 6,452,043 B1
(45) Date of Patent: Sep. 17, 2002

(54) CARBONYLATION OF LOWER ALKYL ALCOHOLS AND THEIR DERIVATIVES USING METALS SUPPORTED ON CARBONIZED POLYSULFONATED DIVINYLBENZENE-STYRENE COPOLYMERS

(75) Inventors: Joseph Robert Zoeller; Andy Hugh Singleton; Gerald Charles Tustin, all of Kingsport; Donald Lee Carver, Church Hill, all of TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/544,639

(22) Filed: Apr. 5, 2000

(51) Int. Cl.[7] ............................ C07C 67/36; C07C 51/12
(52) U.S. Cl. .................. 560/232; 560/175; 560/206; 560/207; 560/233; 562/517; 562/518; 562/519; 562/521; 562/522
(58) Field of Search ................................. 560/232, 175, 560/206, 207, 233; 562/517, 518, 519, 521, 522

(56) References Cited

U.S. PATENT DOCUMENTS

| | | |
|---|---|---|
| 3,689,533 A | 9/1972 | Schultz |
| 3,717,670 A | 2/1973 | Schultz |
| 4,328,125 A | 5/1982 | Drago et al. |
| 4,417,077 A | 11/1983 | Drago et al. |
| 4,776,987 A | 10/1988 | Luft et al. |
| 4,839,311 A | 6/1989 | Maroldo et al. |
| 5,144,068 A | 9/1992 | Smith et al. |
| 5,155,261 A | 10/1992 | Marston et al. |
| 5,360,929 A | 11/1994 | Watston |
| 5,364,963 A | 11/1994 | Minami et al. |
| 5,488,143 A | 1/1996 | Uhm et al. |
| 5,510,524 A | 4/1996 | Garland et al. |
| 5,900,505 A | 5/1999 | Tustin et al. |
| 6,235,673 B1 * | 5/2001 | Zoeller et al. |

FOREIGN PATENT DOCUMENTS

| | | |
|---|---|---|
| EP | 0 120 631 A1 | 10/1984 |
| EP | 0 461 802 A2 | 12/1991 |

OTHER PUBLICATIONS

A. Krzywicki and M. Marczewski, "Formation and Evolution of the Active Site for Methanol Carbonylation on Oxide Catalysts Containing $RhCl_3$", *Journal of Molecular Catalysis*, 6 (1979) pp. 431–440, Netherlands.

H. E. Maneck, D. Gutschick, I. Burkardt, B. Luecke, H. Miessner, and U. Wolf, "Heterogeneous Carbonylation of Methanol on Rhodium Introduced Into Faujasite–Type Zeolites", *Catalysis Today*, 3 (1988) pp. 421–429, Netherlands.

P. Gelin, C. Naccache, and Y. Taarit, "Coordination Chemistry of Rhodium and Iridium in Constrained Zeolite Cavities: Methanol Carbonylation", *Pure & Appl. Chem.*, vol. 8, No. 8, (1988) pp. 1315–1320, Great Britain.

M. J. Howard, M. D. Jones, M. S. Roberts and S. A. Taylor, "$C_1$ to Acetyls: Catalysis and Process", *Catalysis Today*, 18 (1993) pp. 325–354, Amsterdam.

* cited by examiner

*Primary Examiner*—Gary Geist
*Assistant Examiner*—Robert W. Deemie
(74) *Attorney, Agent, or Firm*—Matthew Smith; Bernard Graves

(57) ABSTRACT

A method for producing esters, carboxylic acids and mixtures thereof includes contacting, under carbonylation conditions, lower alkyl alcohols, ethers, lower alkyl alcohol derivatives and mixtures thereof and carbon monoxide with a catalyst having a catalytically effective amount a metal selected from iron, cobalt, nickel, ruthenium, rhodium, palladium, osmium, iridium, platinum, tin and mixtures thereof associated with a carbonized polysulfonated divinylbenzene-styrene copolymer matrix. In a preferred aspect of the invention the method is called out under vapor-phase conditions.

21 Claims, No Drawings

CARBONYLATION OF LOWER ALKYL ALCOHOLS AND THEIR DERIVATIVES USING METALS SUPPORTED ON CARBONIZED POLYSULFONATED DIVINYLBENZENE-STYRENE COPOLYMERS

FIELD OF THE INVENTION

The present invention relates to a method for the carbonylation of alkyl alcohols, ethers and ester-alcohol mixtures to produce their corresponding esters and carboxylic acids. More specifically, the present invention relates to a method for producing acetic acid, methyl acetate and mixtures thereof by the carbonylation of methanol or a methanol source using a catalyst having an active metal specie selected from Fe, Co, Ni, Ru, Rh, Pd, Os, Ir, Pt, and Sn in which the active metal species is supported on a carbonized polysulfonated divinylbenzene-styrenic copolymer resin. A particularly preferred embodiment of the present invention is the aforementioned catalyst used in a vapor-phase carbonylation process for the production of acetic acid, methyl acetate and mixtures thereof.

BACKGROUND OF THE INVENTION

Lower carboxylic acids and esters such as acetic acid and methyl acetate have been known as industrial chemicals for many years. Acetic acid is used in the manufacture of a variety of intermediary and end-products. For example, an important derivative is vinyl acetate which can be used as monomer or co-monomer for a variety of polymers. Acetic acid itself is used as a solvent in the production of terephthalic acid, which is widely used in the container industry, and particularly in the formation of PET beverage containers. There has been considerable research activity in the use of metal catalysts for the carbonylation of lower alkyl alcohols, such as methanol, and ethers to their corresponding carboxylic acids and esters.

Carbonylation of methanol is a well known process for the preparation of carboxylic acids and particularly for producing acetic acid. Such processes are typically carried out in the liquid phase with a catalyst. The prior art teaches the use of a number of catalysts for the synthesis of carboxylic acids by reaction of alcohols with carbon monoxide at elevated temperatures and pressures using a fixed bed reactor in both gas and liquid phase reactions. Generally, the liquid phase carbonylation reaction for the preparation of acetic acid using methanol is performed using homogeneous catalyst systems comprising a Group VIII metal and iodine or an iodine-containing compound such as hydrogen iodide and/or methyl iodide. Rhodium is the most common Group VIII metal catalyst and methyl iodide is the most common promoter. These reactions are conducted in the presence of water to prevent precipitation of the catalyst.

U.S. Pat. No. 5,144,068 describes the inclusion of lithium in the catalyst system which allows the use of less water in the Rh-I homogeneous process. Iridium also is an active catalyst for methanol carbonylation reactions but normally provides reaction rates lower than those offered by rhodium catalysts when used under otherwise similar conditions.

U.S. Pat. No. 5,510,524 teaches that the addition of rhenium improves the rate and stability of both the Ir-I and Rh-I homogeneous catalyst systems.

Schultz, in U.S. Pat. No. 3,689,533, discloses using a supported rhodium heterogeneous catalyst for the carbonylation of alcohols to form carboxylic acids in a vapor phase reaction. Schultz further discloses the presence of a halide promoter.

Schultz in U.S. Pat. No. 3,717,670 describes a supported rhodium catalyst in combination with promoters selected from Groups IB, IIIB, IVB, VB, VIB, VIII, lanthanide and actinide elements of the Periodic Table.

Uhm, in U.S. Pat. No. 5,488,143, describes the use of alkali, alkaline earth or transition metals as promoters for supported rhodium for the halide-promoted, vapor phase methanol carbonylation reaction.

European Patent Applications EP 0 120 631 A1 and EP 0 461 802 A2 describe the use of special carbons as supports for single transition metal component carbonylation catalysts.

The literature contains several reports of the use of rhodium-containing zeolites as vapor phase alcohol carbonylation catalysts at one bar pressure in the presence of halide promoters. The lead references on this type of catalyst are presented by Maneck et al. in *Catalysis Today*, 3 (1988), 421–429. Gelin et al., in *Pure & Appl. Chem.*, Vol 60, No. 8, (1988) 1315–1320, provide examples of the use of rhodium or iridium contained in zeolite as catalysts for the vapor phase carbonylation of methanol in the presence of halide promoter. Krzywicki et al., in *Journal of Molecular Catalysis*, 6 (1979) 431–440, describe the use of silica, alumina, silica-alumina and titanium dioxide as supports for rhodium in the halide-promoted vapor phase carbonylation of methanol, but these supports are generally not as efficient as carbon. Luft et al., in U.S. Pat. No. 4,776,987 and in related disclosures, describe the use of chelating ligands chemically attached to various supports as a means to attach Group VIII metals to a heterogeneous catalyst for the halide-promoted vapor phase carbonylation of ethers or esters to carboxylic anhydrides.

Drago et al., in U.S. Pat. No. 4,417,077, describe the use of anion exchange resins bonded to anionic forms of a single transition metal as catalysts for a number of carbonylation reactions including the halide-promoted carbonylation of methanol.

Unfortunately, these catalysts suffer from the typical difficulties associated with the use of homogeneous catalysis. In particular, upon separation of the catalyst and liquid components, catalyst precipitation and volatilization can occur, particularly if one tries to remove most of the liquid component. Further, mass transfer limitations, which are inherent in the transfer of gaseous carbon monoxide into a liquid reaction medium, limit the ultimate achievable rates in these homogeneously catalyzed processes.

To overcome the problems associated with separation, a number of investigators have attempted to develop heterogeneous processes. U.S. Pat. No. 5,900,505 issued to Tustin, et. al., discloses the carbonylation of methanol to acetic acid using iridium and a second metal as the active components on a support such as activated carbon and inorganic oxides, including silica, alumina, titania, and several zeolites.

Of these active carbonylation catalysts, carbon based supports are generally substantially better from a rate perspective, with Ni, Sn, and Pb displaying negligible activity on inorganic oxides. The normally large difference in rates upon changing from and activated carbon to an inorganic support has been exemplified in M. J. Howard, et. al., *Catalysis Today*, 18, 325 (1993), where, on p. 343, a mixed Rh-Ni catalyst on activated carbon support can be compared to a rhodium on inorganic oxides. With the Rh-Ni on activated carbon, the rate is reported as being ca. 5 mol of acetyl/g of Rh/h at 188° C., 9 bar of 1:2 $CO:H_2$, whereas the range for inorganic oxides is only 0.1 to 0.5 mol of acetyl/g of Rh/h despite being operated at substantially higher temperature (220° C.) and substantially higher CO pressures (40 bar CO pressure).

Although many of the earlier catalysts have been demonstrated to be operable in the liquid phase, the active metal is generally rapidly removed from the support by dissolution in the harsh environments associated with carbonylation of methanol and it derivatives. Attempts to overcome the leaching problem include binding the rhodium to the catalyst using ligands that were chemically bound to a polymer or oxide. For example, U.S. Pat. Nos. 5,155,261; 4,328,125; 5,364,963; and 5,360,929 disclose using tertiary phosphines or other functional groups to retain the rhodium catalyst component on a solid support. Although earlier investigators sought to anchor the rhodium component via ligation, it is now understood that these functional groups are quaternized in the process, forming phosphonium and ammonium salts, and the rhodium, which is present as $Rh(CO)_2I_2^-$, is bound by electrostatic attraction.

Unfortunately, although the catalysts containing functional groups have been successful in retarding the leaching of the Rh catalyst into the liquid phase, they still do not overcome the problems associated with diffusion. Further, the functional groups, present as quaternary salts, and the resin backbones are subject to thermal degradation placing strict constraints on the operating temperatures that can be employed with these catalysts. The inability to use higher temperatures with these functionalized catalysts seriously limits the ultimate attainable rates when they are employed in carbonylation processes.

The much higher rates associated with metals on activated carbon are commercially attractive for a vapor phase carbonylation process. Unfortunately, carbon has several physical limitations which have inhibited its commercial introduction. Although activated carbon is readily available from a number of commercial sources, its characteristics are highly variable, making the generation of reproducible catalysts difficult. Further, activated carbon is brittle and has a poor crush strength. As a consequence, it is subject to rapid physical attrition. The rapid physical attrition requires special catalyst handling. These physical limitations have apparently prevented the introduction of a vapor phase carbonylation process using metals supported on activated carbon despite the attractiveness of such a process.

Therefore, there is a need for a carbonylation process for the production of carboxylic acids and their esters which utilizes a supported metal catalyst which retains the high activity associated with metal catalysts supported on activated carbon, but has greater structural integrity and reproducibility.

SUMMARY OF THE INVENTION

Briefly, the present invention is for a method of producing carboxylic acids and esters from reactants selected from lower alkyl alcohols, ethers, lower alcohol derivative sources and mixtures thereof. The process includes the steps of contacting the reactants with carbon monoxide under carbonylation reaction conditions, and preferably under vapor-phase carbonylation reaction conditions, with at least one solid supported catalyst. The catalyst includes a catalytically effective amount of an active metal selected from iron, cobalt, nickel, ruthenium, rhodium, palladium, osmium, iridium, platinum (i.e., Group VIII metals), tin and mixtures thereof associated with carbonized polysulfonated divinylbenzene-styrene copolymers as a support matrix.

It is an object of the invention to provide a method for producing esters and carboxylic acids. More particularly, it is an object of the present invention to provide a carbonylation method for the production of acetic acid, methyl acetate and mixtures thereof from a lower alkyl alcohol, ethers and lower alcohol derivative sources, preferably where the reactant is methanol.

It is an object of the invention to provide a vapor-phase carbonylation process in which the catalyst is maintained in a solid phase to reduce or eliminate the handling losses of the catalyst.

It is another object of the invention to provide a vapor-phase carbonylation process for the production of acetic acid and methyl acetate which utilizes a more stable catalyst and reduces the need for catalyst recovery and recycle as well as solvent recovery.

These and other objects and advantages of the invention will become apparent to those skilled in the art from the accompanying detailed description.

DETAILED DESCRIPTION OF THE PREFERRED EMBODIMENTS

In accordance with the invention, a process or method for the continuous production of carboxylic acids and esters is provided by contacting, under carbonylation reaction conditions, reactants selected from lower alkyl alcohols, ethers, derivative sources of such lower alkyl alcohols and mixtures thereof, with carbon monoxide and a solid supported carbonylation catalyst. The carbonylation catalyst includes a catalytically effective amount of an active metal selected from iron, cobalt, nickel, ruthenium, rhodium, palladium, osmium, iridium, platinum, tin and mixtures thereof associated with a carbonized polysulfonated divinylbenzene-styrene copolymer as a support matrix. In a preferred embodiment, the process includes a halide containing co-catalyst which is concurrently introduced into the carbonylation reaction with the reactants.

In a particularly preferred embodiment of the present invention, the carbonylation process is operated in the vapor phase and, therefore, is practiced at temperatures above the dew point of the product mixture, i.e., the temperature at which condensation occurs. One skilled in the art understands that the dew point is a complex function of dilution (particularly with respect to non-condensable gases such as unreacted carbon monoxide, hydrogen, or inert diluent gas), product composition, and pressure. Accordingly, the process may be operated over a wide range of temperatures and pressures, provided the temperature exceeds the dew point of the product effluent. In practice, this generally dictates a temperature range of about 100° C. to 500° C., with temperatures in the range of 100° C. to 325° C. being preferred and temperature of about 150° C. to 300° C. being particularly useful. Advantageously, operating in the vapor phase eliminates catalyst dissolution, i.e., metal leaching from the catalyst support, which occurs in the known heterogeneous processes operating in the presence of liquid compounds.

The process of the present invention can likewise be operated over a wide range of pressures, depending upon whether the process is operated under liquid-phase or vapor-phase carbonylation conditions. Suitably, the process can be operated at pressures of from about 0.5–500 bar absolute. In the preferred vapor-phase carbonylation process, the useful pressure range is limited by the dew point of the product mixture. Provided that the carbonylation reaction is operated at a temperature sufficient to prevent liquefaction of the product effluent, pressures can range from about 0.1 to 100 bar absolute. Preferably, the process is carried out at a pressure of from about 0.5 to 50 bars absolute, and most preferably, from about 3 to 30 bar absolute.

Suitable feedstock for the carbonylation process include lower alkyl alcohols, ethers, esters-alcohol mixtures and, as more fully discussed below esters, which may be carbonylated in accordance with the present invention. Non-limiting examples include alcohols and ethers in which an aliphatic carbon atom is directly bonded to an oxygen atom of either an alcoholic hydroxyl group in the compound or an ether oxygen in the compound and may further include aromatic moieties. Preferably, the feedstock is one or more lower alkyl alcohols having from 1 to 10 carbon atoms and preferably having from 1 to 6 carbon atoms, alkane polyols having 2 to 6 carbon atoms, alkyl alkylene polyethers having 3 to 20 carbon atoms and alkoxyalkanols having from 3 to 10 carbon atoms. The most preferred reactant is methanol. Although methanol is preferably used in the process and is normally fed as methanol, it can be supplied in the form of a combination of materials which generate methanol. Examples of such combination of materials include (i) methyl acetate and water and (ii) dimethyl ether and water. In the operation of the process, both methyl acetate and dimethyl ether are formed within the reactor and, unless methyl acetate is the desired product, they are recycled with water to the reactor where they are later consumed to form acetic acid. Thus, one skilled in the art will recognize that it is possible to utilize the present invention to produce carboxylic acid from a corresponding ester feed material.

Although the presence of water in the gaseous feed mixture is not essential when using methanol, the presence of some water is desirable to suppress formation of methyl acetate and/or dimethyl ether. When using methanol to generate acetic acid, the molar ratio of water to methanol can be 0:1 to 10:1, but preferably is in the range of 0.01:1 to 1:1. When using an alternative source of methanol such as methyl acetate or dimethyl ether, the amount of water fed usually is increased to account for the mole of water required for hydrolysis of the methanol alternative. Accordingly, when using either methyl acetate or dimethyl ether, the mole ratio of water to ester or ether is in the range of 1:1 to 10:1, but preferably in the range of 1:1 to 3:1. In the preparation of acetic acid, it is apparent that combinations of methanol, methyl ester, and/or dimethyl ether are equivalent, provided the appropriate amount of water is added to hydrolyze the ether or ester to provide the methanol reactant.

When the process is operated to produce methyl acetate, no water should be added and dimethyl ether becomes the preferred feedstock. Further, when methanol is used as the feedstock in the preparation of methyl acetate, it is necessary to remove water. However, the primary utility of the process of the present invention is in the manufacture of acetic acid.

In the practice of the process of the invention, the reactant is passed through or over a catalyst which includes a catalytically effective amount of an active metal selected from iron, cobalt, nickel, ruthenium, rhodium, palladium, osmium, iridium, platinum (i.e., Group VIII metals) and tin with rhodium and iridium being preferred. The active metal is associated with a support matrix comprising carbonized polysulfonated divinylbenzene-styrene copolymers. These metal components may be used individually or in combination with each other. Optionally, a secondary metallic promoter, particularly the alkali, alkaline earth, the lanthanides, gold, mercury, and transition metals selected from the group V, Nb, Ta, Ti, Zr, Hf, Mo, W, and Re may also be present.

The solid support useful for acting as a carrier for the active metal, and if so utilized the secondary metals described above, is carbonized polysulfonated divinylbenzene-styrene polymers and copolymers having multimodal pore size, including micro and macro pores. Such carbonized polysulfonated divinylbenzene-styrene polymers and copolymers are described in greater detail in U.S. Pat. No. 4,839,331, the disclosure of which is incorporated herein by reference. The carbonized polysulfonated divinylbenzene-styrene support matrix is readily available from Rohm and Haas Company, under the trademark AMBERSORB. Advantageously, the carbonized polysulfonated divinylbenzene-styrene polymers impart exceptional physical properties with regard to hardness and brittleness, but still retain the high catalytic activity (rates) associated with softer activated carbons used in carbonylation processes. These advantageous physical properties permit the process to be operated in any of a variety of reactor designs without sustaining serious losses due to physical attrition.

The compound or form of the active metal(s) used to prepare the catalyst generally is not critical and may be selected such complexes as halides, acetates, nitrates, acetonylacetates, and mixtures thereof. For example, when iridium is the active metal, the catalyst may be prepared from any of a wide variety of iridium containing compounds containing a myriad of combinations of halide, trivalent nitrogen, organic compounds of trivalent phosphorous, carbon monoxide, hydrogen, and 2,4-pentane-dione, either alone or in combination. Such materials are available commercially and may be used in the preparation of the catalysts utilized in the present invention. In addition, the oxides of iridium may be used if dissolved in the appropriate medium. Preferably iridium is a salt of one of its chlorides, such as iridium trichloride or hydrated trichloride, hexacholoroiridate and any of the various salts of hexachloroiridate(IV). One skilled in the art will understand that use of the preferred iridium complexes or other Group VIII and tin metals should be comparable on the basis of cost, solubility, and performance.

Similarly, if so employed, the compound or form of the second metal compound associated with the catalyst generally is not critical, and may be any of a wide variety of compounds containing one or more of the secondary metals. For example, when a metal from the Lanthanide Series is used, it may be present either alone or in combination. A wide variety of compounds of these elements containing various combinations of halides, acetates, nitrates, cyclopentadiene, and 2,4-pentane-dione, either alone or in combination, are available commercially and may be used in the preparation of the catalysts utilized in the process of the present invention, including naturally occurring blends of the Lanthanides. In addition, the oxides of these materials may be used if dissolved in the appropriate medium. Desirably, the compound used to provide the second metal is a water soluble form of the metal(s). Preferred sources include acetates, nitrates, and their halides. The most preferred source among these salts would be dictated by its solubility, preferably water solubility, which can vary widely across this list of useful second components. The most preferred secondary metals include lanthanum, cerium, praseodymium, and neodymium (Atomic numbers 57–60), or combinations thereof. The halides of such preferred secondary metals are generally commercially available and water soluble. Activity is still improved and costs are not necessarily prohibitive when the secondary metal is selected from samarium, europium, gadolinium, terbium, dysprosium, holmium, or erbium (atomic numbers 62–68) and mixtures of thereof.

Desirably, the Group VIII and tin and secondary metal is associated with the support material as a result of soluble impregnation of the metals which may result in either a salt of the metals, an oxide of the metals, or a metal in a free state being deposited on the support.

The amount of active metal, and any secondary metal, associated with the support can each vary from about 0.01 weight % to about 10 weight %, with from about 0.05 weight % to about 5 weight % being preferred and from about 0.1 weight percent to about 2 weight percent of each component being more preferred, wherein the aforementioned weight % is based on the total weight of the supported catalyst.

The preparation of associating the active metal, and if so employed the secondary metal, with the solid support is carried out by preferably dissolving or dispersing the Group VIII and tin (and secondary metal component) in a suitable solvent. The liquid used to deliver the active metal, (Group VIII and tin), and secondary metal in the form a solution, dispersion, or suspension typically is a liquid having a low boiling point, i.e., high vapor pressure at a temperature of from about 10° C. to about 140° C. Examples of suitable solvents include carbon tetrachloride, benzene, acetone, methanol, ethanol, isopropanol, isobutanol, pentane, hexane, cyclohexane, heptane, toluene, pyridine, diethylamine, acetaldehyde, acetic acid, tetrahydrofuran and water. The solid support material is then contacted and desirably impregnated with the metal containing solutions. Various methods of contacting the support material with the Group VIII, tin and secondary metal may be employed. For example, an iridium containing solution can be admixed with a secondary metal solution prior to impregnating the support material. Alternatively, the respective solutions can be impregnated separately into or associated with the support material in series fashion. Desirably, in this alternative embodiment, the support is dried prior to contacting the second solution. Similarly, the Group VIII and tin (and secondary metal) may be associated with the support material in a variety of forms such as using slurries of the Group VIII and tin metal (and secondary metal) can be poured over the support material. Alternatively, the support material may be immersed in excess solutions of the active components with the excess being subsequently removed using techniques known to those skilled in the art. The solvent or liquid is evaporated, i.e. the solid support is dried so that at least a portion of the Group VIII and tin (and secondary metal) is associated with the solid support. Drying temperatures can range from about 100° C. to about 600° C. One skilled in the art will understand that the drying time is dependent upon the temperature, humidity, and solvent. Generally, lower temperatures require longer heating periods to effectively evaporate the solvent from the solid support.

Impregnation is only one means for associating the Group VIII and/or tin component with the solid support matrix. Other suitable methods for preparing the solid support component includes sublimation and plasma deposition. These, and other alternative methods of preparation, are familiar to practitioners of the catalysis art.

In addition to the solid support component, the catalyst can also include a halogen promoter as a second component which may also be catalytically active and which aids in the carbonylation process. The halogen promoter includes one or more of chlorine, bromine and/or iodine and preferably, includes bromine and/or iodine which desirably are vaporous under vapor-phase carbonylation conditions of temperature and pressure. Suitable halides include hydrogen halides such as hydrogen iodide and gaseous hydriodic acid; alkyl and aryl halides having up to 12 carbon atoms such as, methyl iodide, ethyl iodide, 1-iodopropane, 2-iodobutane, 1-iodobutane, methyl bromide, ethyl bromide, and benzyl iodide. Desirably, the halide is a hydrogen halide or an alkyl halide having up to 6 carbon atoms. Non-limiting examples of preferred halides hydrogen iodide, methyl bromide and methyl iodide. The halide may also be a molecular halide such as $I_2$, $Br_2$, or $Cl_2$. The halogen promoter may be introduced at the catalyst preparation step or preferably, is introduced into the carbonylation reactor with the reactants. As a result of contacting the active metal components with the halogen promoter the ultimate active species of the Group VIII and tin and secondary metal may exist as one or more coordination compounds or a halide thereof.

In carrying out the present invention, a mixture, and preferably a gaseous mixture, having lower alkyl alcohols, ethers, and other derivatives of the desired alcohol feedstock; carbon monoxide and, in a preferred embodiment, a halide are fed to a carbonylation reactor containing the Group VIII metal and tin (and secondary metal, if so utilized) supported catalyst described above. The reactor is maintained under carbonylation conditions of temperature and pressure. The process may be operated to produce high proportions of the carboxylic acid or the ester of the carboxylic acid with the feed of the alcohol to obtain high productivity. For example, if acetic acid is the desired product, the feedstock may consist of methyl alcohol, dimethyl ether, methyl acetate, a methyl halide or any combination thereof. If it is desired to increase the proportion of acid produced, the ester may be recycled to the reactor together with water or introduced into a separate reactor with water to produce the acid in a separate zone.

The carbon monoxide can be a purified carbon monoxide or include other gases. The carbon monoxide need not be of a high purity and may contain from about 1% by volume to about 99% by volume carbon monoxide, and preferably from about 70% by volume to about 99% by volume carbon monoxide. The remainder of the gas mixture including such gases as nitrogen, hydrogen, carbon dioxide, water and paraffinic hydrocarbons having from one to four carbon atoms. Although hydrogen is not part of the reaction stoichiometry, hydrogen may be useful in maintaining optimal catalyst activity. The preferred ratio of carbon monoxide to hydrogen generally ranges from about 99:1 to about 2:1, but ranges with even higher hydrogen levels are also likely to be useful.

The amount of halide present to produce an effective carbonylation ranges from a molar ratio of about 1:1 to 10,000:1, with the preferred range being from about 5:1 to about 1000:1, wherein the molar ratio is based on methanol or methanol equivalents to halide.

In a preferred embodiment, the present invention provides a vapor-phase carbonylation method for producing acetic acid, methyl acetate or a mixture thereof which includes the steps of contacting a gaseous mixture comprising methanol, carbon monoxide and, preferably, a halide under vapor-phase carbonylation reaction conditions with a supported catalyst comprising a Group VIII metal, tin or a combination thereof associated with a carbonized polysulfonated divinylbenzene-styrene copolymer support matrix; and recovering the gaseous product which includes acetic acid, methyl acetate or a mixture thereof. Optionally, the catalyst can further include a secondary metal as described above.

The present invention is illustrated in greater detail by the specific examples present below. It is to be understood that these examples are illustrative embodiments and are not intended to be limiting of the invention, but rather are to be construed broadly within the scope and content of the appended claims.

In the examples which follow all of the catalysts were prepared in a similar manner except as specified otherwise.

Catalyst 1 (Rh on AMBERSORB 572)

Rhodium (III) chloride hydrate (282 mg, 1.17 mmol of Rh) was dissolved in 30 mL of distilled water and then added to 20.0 grams of AMBERSORB 572 (obtained from Aldrich Chemical Company) in an evaporating dish. (AMBERSORB is a registered trademark of the Rohm and Haas Corp. used for their commercially available carbonized polysulfonated divinylbenzene-styrene copolymer products having 20–50 mesh size and a surface area of 1100 m$^2$/g.). The mixture was heated using a steam bath and stirred continuously until it became free flowing. The material was transferred to a quartz tube measuring 106 cm long×25 mm (outer diameter). The quartz tube containing the mixture was placed in a three-element electric tube furnace so that the mixture was located in the approximate center of the 61 cm long heated zone of the furnace. Nitrogen was continuously passed through the catalyst bed at a rate of 100 standard cubic centimeters per minute and the tube was heated from ambient temperature to 300° C. over a 2 hour period. The temperature was held at 300° C. for 2 hours. The quartz tube and its contents were allowed to cool back to ambient temperature. The catalyst had a density of 0.47 g/mL and Rh content of 0.55 weight %.

Comparative Catalyst C-1 (Rh On Calgon Activated Carbon)

Rhodium (111) chloride hydrate (282 mg, 1.17 mmol of Ir) was dissolved in 30 mL distilled water and then added to 20.0 grams of 12×40 mesh activated carbon granules, having a BET surface area in excess of 800 m$^2$/g (obtained from Calgon), contained in an evaporating dish. The mixture was heated using a steam bath and stirred continuously until it became free flowing. The material was transferred to a quartz tube measuring 106 cm long×25 mm (outer diameter). The quartz tube containing the mixture was placed in a three-clement electric tube furnace so that the mixture was located in the approximate center of the 61 cm long heated zone of the furnace. Nitrogen was continuously passed through the catalyst bed at a rate of 100 standard cubic centimeters per minute and the tube was heated from ambient temperature to 300° C. over a 2 hour period. The temperature was held at 300° C. for 2 hours. The quartz tube and its contents were allowed to cool back to ambient temperature. The catalyst (Catalyst C-1) had a density of 0.57 g per mL and Rh content of 0.59 weight %.

Catalyst 2 (Ir on AMBERSORB 572)

Catalyst 2 was prepared in the same manner as described for Catalyst 1, except iridium (III) chloride hydrate (418 mg, 1.17 mmol of Ir) was substituted for the rhodium trichloride hydrate. The catalyst had a density of 0.47 g/mL and an Ir content of 1.02 weight %.

Comparative Catalyst C-2 (Ir on Carbon)

Comparative Catalyst C-2 was prepared in the same manner as described for Comparative Catalyst C-1, except iridium (III) chloride hydrate (418 mg, 1.17 mmol of Ir) was substituted for the rhodium trichloride hydrate. The catalyst (Catalyst C-2) had a density of 0.57 g per mL and an Ir content of 1.1 weight %.

Catalyst 3 (Pt on AMBERSORB 572)

Catalyst 3 was prepared in the same manner as described for Catalyst 1, except chloroplatinic acid hexahydrate ($H_2PtCl_6.6H_2O$, 580 mg, 1.17 mmol of Pt) was substituted for the rhodium trichloride trihydrate. The catalyst had a density of 0.47 g/mL and a Pt content of 0.95 weight %.

Comparative Catalyst C-3 (Pt on Carbon)

Comparative Catalyst C-3 was prepared in the same manner as described for Comparative Catalyst C-1, except chloroplatinic acid hexahydrate ($H_2PtCl_6.6H_2O$, 580 mg, 1.17 mmol of Pt) was substituted for the rhodium trichloride trihydrate. The catalyst (Catalyst C-3) had a density of 0.57 g per mL and a Pt content of 1.10 weight %.

Catalyst 4 (Sn on AMBERSORB 572)

Tin (II) chloride dihydrate (263 mg, 1.17 mmol of Sn) was dissolved in a solution of 5 mL concentrated hydrochloric acid and 30 mL distilled water. The resultant solution was then added to 20.0 grams of AMBERSORB 572 (obtained from Aldrich Chemical Company) in an evaporating dish. The mixture was heated using a steam bath and continuously stirred until it became free flowing. The material was transferred to a quartz tube measuring 106 cm long×25 mm (outer diameter). The quartz tube containing the mixture was placed in a three-element electric tube furnace so that the mixture was located in the approximate center of the 61 cm long heated zone of the furnace. Nitrogen was continuously passed through the catalyst bed at a rate of 100 standard cubic centimeters per minute and the tube was heated from ambient temperature to 300° C. over a 2 hour period. The temperature was held at 300° C. for 2 hours. The quartz tube and its contents were allowed to cool back to ambient temperature. The catalyst had a density of 0.47 g/mL and tin content of 0.63 weight %.

Comparative Catalyst C-4 (Sn on Carbon)

Tin (II) chloride dihydrate (282 mg, 1.17 mmol of Ir) was dissolved in a solution of 5 mL concentrated hydrochloric acid in 30 mL of distilled water. The solution was then added to 20.0 g rams of 12×40 mesh activated carbon granules (obtained from Calgon having a BET surface area in excess of 800 m$^2$/g) contained in an evaporating dish. The mixture was heated using a steam bath and stirred continuously until it became free flowing. The material was then transferred to a quartz tube measuring 106 cm long×25 mm (outer diameter). The quartz tube containing the mixture was placed in a three-element electric tube furnace so that the mixture was located in the approximate center of the 61 cm long heated zone of the furnace. Nitrogen was continuously passed through the catalyst bed at a rate of 100 standard cubic centimeters per minute and the tube was heated from ambient temperature to 300° C. over a 2 hour period. The temperature was held at 300° C. for 2 hours. The quartz tube and its contents were allowed to cool back to ambient temperature. The catalyst (Catalyst C-4) had a density of 0.57 g per mL and a Sn content of 0.58 weight %.

Carbonylation of Methanol—Vapor Phase Process

The reactor system consisted of a 800 to 950 mm (31.5 and 37 inch) section of 6.35 mm (¼ inch) diameter tubing constructed of Hastelloy alloy. The upper portion of the tube constituted the preheat and reaction (carbonylation) zones which were assembled by inserting a quartz wool pad 410 mm from the top of the reactor to act as support for the catalyst, followed sequentially by (1) a 0.7 g bed of fine quartz chips (840 microns), (2) either 1.0 mL (0.47 g) of the AMBERSORB 572 supported catalyst, or 0.5 g (0.88 mL) of the activated carbon supported catalyst in the case of the activated carbon, wherein the preparation of these catalysts appear in the preceding Examples, and (3) an additional 6 grams of fine quartz chips. The top of the tube was attached to an inlet manifold for introducing liquid and gaseous feeds.

The six (6) grams of fine quartz chips acted as a heat exchange surface to vaporize the liquid feeds. Care was taken not to allow any liquid feeds to contact the catalyst bed at any time, including assembly, start-up, operation, and shutdown. The remaining lower length of tubing (product recovery section) consisted of a vortex cooler which varied in length depending on the original length of tubing employed and was maintained at approximately 0–5° C. during operation.

The gases were fed using Brooks flow controllers and liquids were fed using a high performance liquid chromatography pump. The gaseous products leaving the reaction zone were condensed using the vortex cooler described above operating at 0–5° C. The product reservoir was a tank placed downstream from the reactor system. The pressure was maintained using a Tescom 44-2300 Regulator on the outlet side of the reactor system and the temperature of the reaction section was maintained using heating tape on the outside of the reaction system.

Feeding of hydrogen and carbon monoxide to the reactor was commenced while maintaining the reactor at a temperature of 240° C. and a pressure of 17.2 bara (250 psia). The flow rate of hydrogen was set at 25 standard cubic cm. per minute (cc/min) and the carbon monoxide flow rate was set at 100 cc/min. The reactor section was maintained under these conditions for 1 hour or until the temperature and pressure had stabilized (whichever was longer.) The high pressure liquid chromatography pump was then started, feeding a mixture consisting of 70 weight percent methanol and 30 weight percent methyl iodide at a rate of 12 ml/hr (The solution had a density of 1 g/mL.) Samples of the liquid product were collected and analyzed periodically using gas chromatographic techniques.

The comparative examples using activated carbon based catalysts were run in a similar fashion, except they utilized 0.5 grams (0.88 mL) of catalyst.

CARBONYLATION EXAMPLE 1

The composition and weight of the samples taken periodically during the procedure described above in which Catalyst 1, consisting of Rh on AMBERSORB 572, was used are set forth in Table 1 below wherein "Time" is the total time of operation (in hours) of the carbonylation commencing with the feeding of the methanol until a particular sample was taken. The values set forth below "MeI" (methyl iodide), "MeOAc" (methyl acetate), "MeOH" (methanol) and "AcOH" (acetic acid) are weight percentages of each of those compounds present in the sample. The weight of each sample is given in grams.

TABLE 1

| Sample Number | Expired Time (h) | Sample (Wt %) | | | | Sample Weight (g) |
|---|---|---|---|---|---|---|
| | | MeI | MeOAc | MeOH | AcOH | |
| 1 | 3.50 | 13.32 | 35.38 | 10.95 | 25.17 | 37.2 |
| 2 | 7.50 | 13.54 | 35.54 | 11.02 | 24.98 | 49 |
| 3 | 10.50 | 13.02 | 34.71 | 10.58 | 25.2 | 36.9 |
| 4 | 15.50 | 11.24 | 35.14 | 11.39 | 25.82 | 61.2 |
| 5 | 17.50 | 12.92 | 41.96 | 9.00 | 19.8 | 25.1 |

TABLE 1-continued

| Sample Number | Expired Time (h) | Sample (Wt %) | | | | Sample Weight (g) |
|---|---|---|---|---|---|---|
| | | MeI | MeOAc | MeOH | AcOH | |
| 6 | 23.50 | 13.82 | 43.03 | 8.74 | 20.01 | 73.1 |
| 7 | 27.50 | 13.5 | 42.01 | 8.86 | 19.47 | 48.9 |
| 8 | 31.50 | 14.42 | 42.65 | 9.08 | 19.8 | 49.1 |
| 9 | 34.50 | 13.44 | 44.12 | 9.46 | 20.04 | 36.9 |
| 10 | 39.50 | 13.92 | 43.92 | 9.28 | 19.85 | 60.6 |
| 11 | 41.50 | 13.52 | 42.4 | 8.81 | 19.85 | 25.4 |
| 12 | 47.50 | 13.71 | 43.24 | 9.11 | 20.08 | 73.2 |
| 13 | 51.50 | 12.83 | 32.75 | 1.35 | 43.29 | 49.1 |
| 14 | 55.50 | 12.66 | 32.42 | 1.32 | 42.7 | 48.9 |
| 15 | 58.50 | 12.63 | 32.87 | 1.37 | 43.34 | 36.9 |
| 16 | 63.50 | 12.73 | 39.73 | 7.59 | 28.8 | 60.2 |
| 17 | 65.50 | 13.14 | 39.7 | 7.29 | 28.31 | 25.4 |
| 18 | 71.50 | 12.8 | 38.77 | 7.22 | 28 | 73.1 |
| 19 | 75.50 | 13.82 | 40.58 | 7.54 | 29.35 | 49.2 |
| 20 | 79.50 | 12.53 | 38.55 | 7.12 | 27.73 | 24.2 |

The rate of acetyl production based on the preceding experiment utilizing Catalyst 1 is set fourth in Table 2 below wherein Sample Number and Time values correspond to those of Table 1. "Acetyl Produced" is the amount (millimoles) of methyl acetate and acetic acid produced during each increment of Time calculated from the formula:

Sample Weight×10×((Weight % McOAc/74)+(Weight % AcOH/60))

"Production Rate" is the moles of Acetyl Produced per liter of catalyst volume per hour during each increment of Time (Time Increment), i.e., the time of operation between samples. The formula for determining moles of Acetyl Produced per liter of catalyst volume per hour is:

(mmol Acetyl Produced)/(vol. of catalyst (mL)×Time Increment)

wherein the volume of catalyst used was 1.0 mL. (Note: the comparative examples, which had a significantly higher density, used 0.88 mL of catalyst.)

TABLE 2

| Sample Number | Expired Time (hours) | Acetyl Produced (mmol) | Rate (mol/L-h) |
|---|---|---|---|
| 1 | 3.50 | 333.9 | 95.4 |
| 2 | 7.50 | 439.3 | 109.8 |
| 3 | 10.50 | 328.1 | 109.4 |
| 4 | 15.50 | 554.0 | 110.8 |
| 5 | 17.50 | 225.2 | 112.6 |
| 6 | 23.50 | 668.9 | 111.5 |
| 7 | 27.50 | 436.3 | 109.1 |
| 8 | 31.50 | 445.0 | 111.3 |
| 9 | 34.50 | 343.2 | 114.4 |
| 10 | 39.50 | 560.2 | 112.0 |
| 11 | 41.50 | 229.6 | 114.8 |
| 12 | 47.50 | 672.7 | 112.1 |
| 13 | 51.50 | 571.6 | 142.9 |
| 14 | 55.50 | 562.2 | 140.6 |
| 15 | 58.50 | 430.4 | 143.5 |
| 16 | 63.50 | 612.2 | 122.4 |
| 17 | 65.50 | 256.1 | 128.1 |
| 18 | 71.50 | 724.1 | 120.7 |
| 19 | 75.50 | 510.5 | 127.6 |
| 20 | 79.50 | 237.9 | 59.5 |

The total production of acetyl products (acetic acid+ methyl acetate) over the 79.5 hr experiment was 9.14 moles representing a space time yield of 115 mol/L-h (245 mol/ $kg_{cat}$-h) and a Rh turnover frequency of 76.3 mol of acetyl/ mol Rh/min.

COMPARATIVE CARBONYLATION EXAMPLE C-1

Carbonylation Example 2 was repeated except that 0.5 g of Comparative Catalyst C-1 was used. The results are summarized in Tables 3 and 4.

TABLE 3

| Sample Number | Expired Time (h) | Sample (Wt %) | | | | Sample Weight (g) |
|---|---|---|---|---|---|---|
| | | MeI | MeOAc | MeOH | AcOH | |
| 1 | 4.00 | 15.27 | 38.87 | 3.4 | 30.27 | 26.9 |
| 2 | 6.00 | 15.86 | 39.8 | 3.46 | 30.93 | 24.9 |
| 3 | 7.00 | 14.36 | 27.85 | 1.29 | 47.57 | 20 |
| 4 | 8.00 | 14.45 | 26.92 | 1.24 | 46.16 | 19.1 |
| 5 | 10.00 | 13.64 | 27.07 | 1.26 | 47.05 | 24.2 |
| 6 | 15.50 | 14.55 | 22.12 | 0.43 | 53 | 90.1 |
| 7 | 17.50 | 14.52 | 22.2 | 0.44 | 53.18 | 29.1 |
| 8 | 23.00 | 13.59 | 11.86 | 0.09 | 65.74 | 85.9 |
| 9 | 25.00 | 13.42 | 11.85 | 0.09 | 65.62 | 28.1 |
| 10 | 27.00 | 13.46 | 12.03 | 0.1 | 66.41 | 26.5 |
| 11 | 29.00 | 14.59 | 15.35 | 0.47 | 62.63 | 25.9 |
| 12 | 31.00 | 13.49 | 14.83 | 0.47 | 61.87 | 25.6 |
| 13 | 33.00 | 13.78 | 16.85 | 0.2 | 60.31 | 25.8 |
| 14 | 34.00 | 14.08 | 16.77 | 0.22 | 60.59 | 8.9 |

TABLE 4

| Sample Number | Expired Time (h) | Acetyl Produced (mmol) | Rate (mol/L-h) |
|---|---|---|---|
| 1 | 4.00 | 277.0 | 78.9 |
| 2 | 6.00 | 262.3 | 149.5 |
| 3 | 7.00 | 233.8 | 266.6 |
| 4 | 8.00 | 216.4 | 246.7 |
| 5 | 10.00 | 278.3 | 158.6 |
| 6 | 15.50 | 1065.2 | 220.8 |
| 7 | 17.50 | 345.2 | 196.8 |
| 8 | 23.00 | 1078.8 | 223.6 |
| 9 | 25.00 | 352.3 | 200.8 |
| 10 | 27.00 | 336.4 | 191.7 |
| 11 | 29.00 | 324.1 | 184.7 |
| 12 | 31.00 | 315.3 | 179.7 |
| 13 | 33.00 | 318.1 | 181.3 |
| 14 | 34.00 | 110.0 | 125.5 |

The total production of acetyl products (acetic acid+ methyl acetate) over the 34.0 hr experiment was 5.51 moles representing a space time yield of 184 mol/L-h (322 mol/$kg_{cay}$-h) and a Rh turnover frequency of 94.2 mol of acetyl/mol Rh/min.

CARBONYLATION EXAMPLE 2

Carbonylation Example 1 was repeated except that Catalyst 2 (1.1% Ir on AMBERSORB 572) was used in place of Catalyst 1. The process was operated for 58.5 hours and generated 4.68 moles of acetyl products, representing a space time yield of 80 mol/L-h (170 mol/$kg_{cat}$-h) and an Ir turnover frequency of 50.2 mol of acetyl/mol Ir/min.

COMPARATIVE CARBONYLATION EXAMPLE C-2

Comparative Carbonylation Example C-1 was repeated using Comparative Catalyst C-2 (1.1% Ir on carbon) instead of Comparative Catalyst C-1. The process was operated for 180 hours and generated 8.65 moles of acetyl products, representing a space time yield of 55 mol/L-h (96 mol/$kg_{cat}$-h) and an Ir turnover frequency of 28.0 mol of acetyl/mol Ir/min.

CARBONYLATION EXAMPLE 3

Carbonylation Example 1 was repeated except that Catalyst 3 (0.95% Pt on AMBERSORB 572) was used in place of Catalyst 1. The process was operated for 71 hours and generated 0.95 moles of acetyl products, representing a space time yield of 13.4 mol/L-h (28.5 mol/$kg_{cat}$-h) and a Pt turnover frequency of 9.1 mol of acetyl/mol Pt/min.

COMPARATIVE CARBONYLATION EXAMPLE C-3

Comparative Carbonylation Example C-1 was repeated using Comparative Catalyst C-3 (Pt on carbon) instead of Comparative Catalyst C-1. The process was operated for 50 hours and generated 2.23 moles of acetyl products, representing a space time yield of 45 mol/L-h (89 mol/$kg_{cat}$-h) and a Pt turnover frequency of 26.4 mol of acetyl/mol Pt/min.

CARBONYLATION EXAMPLE 4

Carbonylation Example 1 was repeated, except that Catalyst 4 (0.63% Sn on AMBERSORB 572) was used in place of Catalyst 1. The results of this carbonylation example are summarized in Tables 5 and 6.

TABLE 5

| Sample Number | Expired Time (h) | Sample (Wt %) | | | | Sample Weight (g) |
|---|---|---|---|---|---|---|
| | | MeI | MeOAc | MeOH | AcOH | |
| 1 | 3.50 | 18.31 | 0.97 | 72.64 | 3.06 | 35.9 |
| 2 | 7.50 | 19.61 | 0.97 | 76.73 | 3.16 | 50.1 |
| 3 | 10.50 | 17.96 | 1 | 74.8 | 3.15 | 37.1 |
| 4 | 15.50 | 16.71 | 1.03 | 75.53 | 3.1 | 61.9 |
| 5 | 17.50 | 22.25 | 5.89 | 68.93 | 0.43 | 25.1 |
| 6 | 23.50 | 22 | 6.01 | 67.46 | 0.5 | 72.9 |
| 7 | 27.50 | 21.53 | 5.78 | 64.51 | 0.44 | 48.9 |
| 8 | 31.50 | 21.9 | 5.92 | 67.81 | 4.55 | 48.3 |
| 9 | 34.50 | 22.38 | 5.97 | 68.26 | 4.58 | 36.5 |
| 10 | 39.50 | 20.87 | 5.89 | 65.77 | 4.35 | 60.2 |
| 11 | 41.50 | 20.51 | 5.8 | 68.94 | 4.49 | 25.1 |
| 12 | 47.50 | 21.62 | 6.12 | 69.02 | 4.71 | 73.5 |
| 13 | 51.50 | 6.8 | 5.41 | 79.95 | 0.64 | 49.3 |
| 14 | 55.50 | 21.89 | 11.13 | 62.79 | 0.85 | 49.6 |
| 15 | 58.50 | 22.35 | 11.35 | 62.88 | 0.84 | 36.7 |
| 16 | 63.50 | 21.36 | 10.91 | 60.67 | 0.82 | 62.2 |
| 17 | 65.50 | 21.15 | 12.14 | 59.63 | 0.64 | 25.6 |
| 18 | 71.50 | 20.71 | 11.99 | 59.17 | 0.61 | 72.9 |
| 19 | 75.50 | 20.37 | 11.89 | 58.11 | 0.59 | 49.1 |

TABLE 6

| Sample Number | Expired Time (h) | Acetyl Produced (mmol) | Rate (mol/L-h) |
|---|---|---|---|
| 1 | 3.50 | 23.0 | 6.6 |
| 2 | 7.50 | 33.0 | 8.2 |
| 3 | 10.50 | 24.5 | 8.2 |
| 4 | 15.50 | 40.6 | 8.1 |
| 5 | 17.50 | 21.8 | 10.9 |
| 6 | 23.50 | 65.3 | 10.9 |
| 7 | 27.50 | 41.8 | 10.4 |
| 8 | 31.50 | 75.3 | 18.8 |
| 9 | 34.50 | 57.3 | 19.1 |
| 10 | 39.50 | 91.6 | 18.3 |
| 11 | 41.50 | 38.5 | 19.2 |
| 12 | 47.50 | 118.5 | 19.7 |
| 13 | 51.50 | 41.3 | 10.3 |
| 14 | 55.50 | 81.6 | 20.4 |
| 15 | 58.50 | 61.4 | 20.5 |
| 16 | 63.50 | 100.2 | 20.0 |
| 17 | 65.50 | 44.7 | 22.4 |
| 18 | 71.50 | 125.5 | 20.9 |
| 19 | 75.50 | 83.7 | 20.9 |

This catalyst was unique among all the carbonylation and comparative carbonylation examples in that it displayed an induction period and did not reach a steady production rate until the catalyst was in use for nearly 28 hours. After reaching steady state, the reaction was operated for an additional 48 hours, producing 0.920 moles of acetyl units, representing a space time yield of 19.2 mol/l-h (40.8 mol/$kg_{cat}$-h) and a tin turnover frequency of 13.9 mol of acetyl/mol Sn/min.

COMPARATIVE CARBONYLATION EXAMPLE C-4

Comparative Carbonylation Example C-1 was repeated using Comparative Catalyst C-4 (Sn on carbon) instead of Comparative Catalyst C-1. The process was operated for 3.45 hours and generated 2.05 moles of acetyl products, representing a space time yield of 68 mol/L-h (118 mol/$kg_{cat}$-h) and an tin turnover frequency of 40.5 mol of acetyl/mol/min.

Although the present invention has been shown and described in terms of the presently preferred embodiments, it is to be understood that various modifications and substitutions, rearrangements of parts, components and process steps can be made by those skilled in the art without departing from the spirit and scope of the invention.

We claim:

1. A method for producing esters, carboxylic acids and mixtures thereof from reactants comprising lower alkyl alcohols, ethers, lower alkyl alcohol derivatives and mixtures thereof, said process comprising contacting the reactants and carbon monoxide with a catalyst under carbonylation conditions wherein said catalyst includes a catalytically effective amount a metal selected from the group consisting of iron, cobalt, nickel, ruthenium, rhodium, palladium, osmium, iridium, platinum, tin and mixtures thereof associated with a carbonized polysulfonated divinylbenzene-styrene copolymer matrix.

2. The method of claim 1 wherein said reactants are selected from the group consisting of lower alkyl alcohols having from 1 to 10 carbon atoms, alkane polyols having 2 to 6 carbon atoms, alkyl alkylene polyethers having 3 to 20 carbon atoms and alkoxyalkanols having from 3 to 10 carbon atoms and mixtures thereof.

3. The method of claim 1 wherein said reactant is selected from the group consisting of methanol, methyl acetate, dimethyl ether and mixtures thereof.

4. The method of claim 1 wherein said esters and carboxylic acids produced include acetic acid, methyl acetate and mixtures thereof.

5. The method of claim 1 further comprising concurrently contacting said reactants with a halide compound selected from the group consisting of chlorine, bromine, iodine and combinations thereof.

6. The method of claim 5 wherein said wherein said halide is selected from the group consisting of hydrogen iodide, gaseous hydriodic acid; alkyl and aryl iodides having up to 12 carbon atoms selected from the group consisting of methyl iodide, ethyl iodide, 1-iodopropane, 2-iodobutane, 1-iodobutane, benzyl iodide, hydrogen bromide, methyl bromide and mixtures thereof.

7. The method of claim 6 wherein said halide is selected from the group consisting of iodine, hydrogen iodide, methyl iodide, bromine, hydrogen bromide, methyl bromide and mixtures thereof.

8. The method of claim 1 wherein said carbonylation condition is a vapor-phase having a temperature of about 100° C. to 350° C. and a pressure of about 1 to 50 bar absolute.

9. The method of claim 1 wherein said catalyst has from about 0.01 weight % to about 10 weight % of said metal associated with said carbonized polysulfonated divinylbenzene-styrene copolymer matrix.

10. The method of claim 9 wherein said catalyst has from about 0.1 weight % to about 2 weight % metal associated with said carbonized polysulfonated divinylbenzene-styrene copolymer matrix.

11. The method of claim 1 wherein said catalyst further includes a secondary metal selected from the group consisting of alkali, alkaline earth, lanthanides, gold, mercury, and transition metals selected from the group consisting of V, Nb, Ta, Ti, Zr, Hf, Mo, W, Re and mixtures thereof.

12. A vapor-phase carbonylation method for preparing acetic acid, methyl acetate and mixtures thereof comprising the steps of:
a. contacting a gaseous mixture comprising methanol and carbon monoxide with a catalyst comprising a catalytically effective amount of a metal selected from the group consisting of iron, cobalt, nickel, ruthenium, rhodium, palladium, osmium, iridium, platinum, tin and mixtures thereof associated with a carbonized polysulfonated divinylbenzene-styrene copolymer matrix; and
b. recovering acetic acid, methyl acetate or a mixture thereof from the gaseous product.

13. The method of claim 12 further comprising concurrently contacting said reactants with a halide compound selected from the group consisting of hydrogen iodide, gaseous hydriodie acid; alkyl and aryl iodides having up to 12 carbon atoms selected from the group consisting of methyl iodide, ethyl iodide, 1-iodopropane, 2-iodobutane, 1-iodobutane, benzyl iodide, hydrogen bromide, methyl bromide and mixtures thereof.

14. The method of claim 13 wherein said halide is selected from the group consisting of iodine, hydrogen iodide, methyl iodide, bromine, hydrogen bromide, methyl bromide and mixtures thereof.

15. The method of claim 12 wherein said catalyst further includes a secondary metal selected from the group consisting of alkali, alkaline earth, lanthanides, gold, mercury, and transition metals selected from the group consisting of V, Nb, Ta, Ti, Zr, Hf, Mo, W, Re and mixtures thereof and wherein the amount of said metal and secondary metal associated with said carbonized polysulfonated divinylbenzene-styrene copolymer matrix independently ranges from about 0.01 weight % to about 10 weight %, based on the total weight of the catalyst.

16. The method of claim 15 wherein the amount of said metals associated with said carbonized polysulfonated divinylbenzene-styrene copolymer independently ranges from about 0.05 weight % to about 5 weight %.

17. The method of claim 15 wherein the amount of said metals associated with said carbonized polysulfonated divinylbenzene-styrene copolymer independently ranges from about 0.1 weight percent to about 2 weight percent of each component being more preferred.

18. A vapor-phase carbonylation method for preparing acetic acid, methyl acetate and mixtures thereof comprising the steps of:
a. contacting a gaseous mixture comprising methanol, carbon monoxide and a halide with a catalyst comprising from about 0.01 weight % to about 10 weight %, based on the total weight of the catalyst, of a metal selected from the group consisting of iron, cobalt, nickel, ruthenium, rhodium, palladium, osmium, iridium, platinum, tin and mixtures thereof associated with a carbonized polysulfonated divinylbenzene-styrene copolymer matrix; and
b. recovering acetic acid, methyl acetate or a mixture thereof from the gaseous product.

19. The method of claim 18 wherein said catalyst further includes a secondary metal selected from the group consisting of alkali, alkaline earth, lanthanides, gold, mercury, and transition metals selected from the group consisting of V, Nb, Ta, Ti, Zr, Hf, Mo, W, Re and mixtures thereof and wherein the amount of said metal and secondary metal associated with said carbonized polysulfonated divinylbenzene-styrene copolymer matrix independently ranges from about 0.05 weight % to about 5 weight %, based on the total weight of the catalyst.

20. The method of claim 18 wherein said halide is selected from the group consisting of iodine, hydrogen iodide, methyl iodide, bromine, hydrogen bromide, methyl bromide and mixtures thereof.

21. The method of claim 19 wherein said secondary metal is selected from the group consisting of lanthanum, cerium, praseodymium, neodymium, their respective salts and mixtures thereof.

* * * * *

UNITED STATES PATENT AND TRADEMARK OFFICE
CERTIFICATE OF CORRECTION

PATENT NO.    : 6,452,043 B1
DATED         : September 17, 2002
INVENTOR(S)   : Joseph Robert Zoeller, Andy Hugh Singleton, Gerald Charles Tustin and Donald Lee Carver It is certified that error appears in the above-identified patent and that said Letters Patent is hereby corrected as shown below:

Column 6,
Line 32, "hexachloroiridatc" should read -- hexachloroiridate --.

Column 9,
Line 32, "three-clement" should read -- three-element --.

Column 10,
Line 8, "$H_2PtCl_6 \cdot 6H_2O$" should read -- $H_2PtCl_6 \bullet 6H_2O$ --.

Column 11,
Line 53, "MeI" should read -- MeI --.

Column 12,
Lines 27-28, "McOAc/74" should read -- MeOAc/74 --.

Column 13,
Lines 44-45, "(322 mol/$Kg_{cay}$-h)" should read -- (322 mol/$Kg_{cat}$-h) --.

Signed and Sealed this

Tenth Day of December, 2002

JAMES E. ROGAN
*Director of the United States Patent and Trademark Office*